United States Patent
Sugawara

(10) Patent No.: US 11,261,374 B2
(45) Date of Patent: Mar. 1, 2022

(54) SQUARYLIUM COMPOUND, LIGHT-EMITTING COMPOSITION, AND LIGHT-EMITTING FILM

(71) Applicant: Konica Minolta, Inc., Tokyo (JP)

(72) Inventor: Ryutaro Sugawara, Machida (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 17/275,912

(22) PCT Filed: Sep. 2, 2019

(86) PCT No.: PCT/JP2019/034329
§ 371 (c)(1),
(2) Date: Mar. 12, 2021

(87) PCT Pub. No.: WO2020/054472
PCT Pub. Date: Mar. 19, 2020

(65) Prior Publication Data
US 2021/0261858 A1      Aug. 26, 2021

(30) Foreign Application Priority Data

Sep. 14, 2018   (JP) .............................. JP2018-172404

(51) Int. Cl.
*C07C 211/54*   (2006.01)
*C09K 11/06*   (2006.01)

(52) U.S. Cl.
CPC ............ *C09K 11/06* (2013.01); *C07C 211/54* (2013.01); *C07C 2601/04* (2017.05); *C07C 2601/16* (2017.05); *C09K 2211/1007* (2013.01)

(58) Field of Classification Search
CPC ............ C09K 11/06; C09K 2211/1007; C07C 211/54; C07C 2601/16; C07C 2601/04
See application file for complete search history.

(56) References Cited

U.S. PATENT DOCUMENTS

| | | | | |
|---|---|---|---|---|
| 5,169,987 A | * | 12/1992 | Akasaki ................ | C07C 225/22 548/440 |
| 5,230,975 A | * | 7/1993 | Law ..................... | C07C 217/80 430/123.43 |
| 10,333,079 B2 | * | 6/2019 | Thompson .......... | H01L 51/0059 |
| 2019/0196073 A1 | * | 6/2019 | Samejima ............ | G02B 1/04 |

FOREIGN PATENT DOCUMENTS

| | | | | |
|---|---|---|---|---|
| JP | 63132246 A | * | 6/1988 | ........... G03G 5/0611 |
| JP | 01146846 A | * | 6/1989 | ........... G03G 5/0611 |
| JP | 2014169284 A | * | 9/2014 | |
| WO | WO-2012109232 A2 | * | 8/2012 | ............. B82Y 10/00 |

OTHER PUBLICATIONS

S. Wang et al., 23 Chemistry of Materials, 4789-4798 (2011) (Year: 2011).*
International Preliminary Report on Patentability and Written Opinion of the International Searching Authority for International Application No. PCT/JP2019/034329; dated Mar. 9, 2021.
Wang, Siyi, "N,N-Diarylanilinosquaraines and Their Application to Organic Photovoltaics", Chemistry of Materials, 2011; vol. 23; pp. 4789-4798.
International Search Report for International Application No. PCT/JP2019/034329; dated Nov. 12, 2019.

* cited by examiner

*Primary Examiner* — Alexander R Pagano
(74) *Attorney, Agent, or Firm* — Cantor Colburn LLP

(57) ABSTRACT

The present invention addresses the issue of providing: a novel squarylium compound that has high light-emission efficiency, in particular little reduction in light-emission efficiency in a solid membrane, and is capable of emitting a near-infrared light having excellent light resistance; and a light-emitting composition and a light-emitting film that contain said squarylium compound. This squarylium compound is characterized by having a structure indicated by general formula (1).

General formula (1)

6 Claims, No Drawings

SQUARYLIUM COMPOUND, LIGHT-EMITTING COMPOSITION, AND LIGHT-EMITTING FILM

CROSS REFERENCE TO RELATED APPLICATIONS

This is the U.S. national stage of application No. PCT/JP2019/034329, filed on Sep. 2, 2019. Priority under 35 U.S.C. § 119(a) and 35 U.S.C. § 365(b) is claimed from Japanese Application No. 2018-172404, filed Sep. 14, 2018, the disclosure of which is also incorporated herein by reference.

TECHNICAL FIELD

The present invention relates to a novel squarylium compound, a light-emitting composition and a light-emitting film. More specifically, the present invention relates to a novel squarylium compound capable of emitting near-infrared light having high luminous efficiency and excellent light resistance, a light-emitting composition and a light-emitting film each containing the squarylium compound.

BACKGROUND

In recent years, near-infrared light emitting materials have attracted a great deal of attention from the viewpoint of their use in infrared cameras, bioimaging, biosensing, and infrared communication. For example, a pulse oximeter, which is one of biological sensing, uses near-infrared light to calculate the oxygen saturation in blood. It is also being studied as a sensitizer for organic solar cells. With the expansion of the fields of use of near-infrared light, the performance required for near-infrared light emitting materials, particularly the light emission property, the robustness such as light resistance and chemical resistance, is becoming stricter.

The emission wavelength suitable for each application varies, but when used for biological sensing, a material having a high brightness in a wavelength band called a "biological window" having a wavelength of 650 to 900 nm, which easily transmits a living body, is preferably used. When photoexcited from the outside, a material having a high molar extinction coefficient and excellent light resistance is required.

However, the compounds that emit light in the near-infrared region are difficult to design and synthesize, therefore, development of the compounds has not progressed much. As examples of the compounds, Non-Patent Document 1 describes squarylium compounds R-1 and R-2 having the following structures.

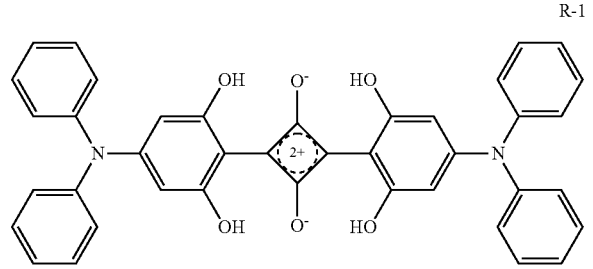

R-1

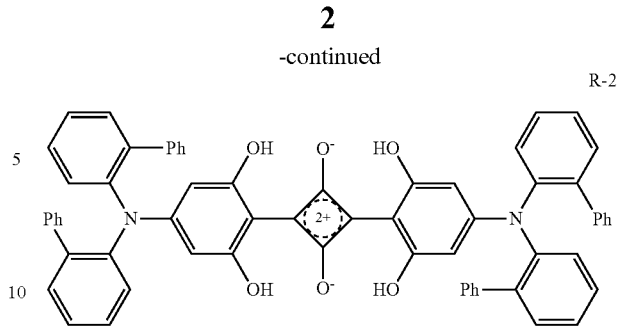

R-2

Non-Patent Document 1 describes that the squarylium compound emits fluorescence in the near-infrared region in a solution. However, when the present inventor evaluated the above squarylium compound described in Non-Patent Document 1 in a solid film, the luminous efficiency and light resistance were not fully satisfactory.

PRIOR ART DOCUMENTS

Non-Patent Document

Non-Patent Document 1: S. Wang, et al., Chem. Mater, 2011, 23, 4789-4798.

SUMMARY OF THE INVENTION

Problems to be Solved by the Invention

The present invention has been made in view of the above problems and situations. An object of the present invention is to provide a novel squarylium compound which is capable of emitting infrared light having high luminous efficiency, particularly little decrease in luminous efficiency in a solid film, and excellent light resistance. Another object of the present invention is to provide a light-emitting composition and a light-emitting film each containing the squarylium compound.

Means to Solve the Problems

As a result of examining the causes of the above problems in order to solve the above problems, the present inventors have found the following. That is, by using a squarylium compound having a specific structure having a substituent at an ortho position of an arylamine, the present inventors have found a novel squarylium compound capable of emitting near-infrared light having high luminous efficiency, particularly little decrease in luminous efficiency in a solid film, and excellent light resistance. Thus, the present invention has been achieved.

The above problem according to the present invention is solved by the following means.

1. A squarylium compound having a structure represented by Formula (1).

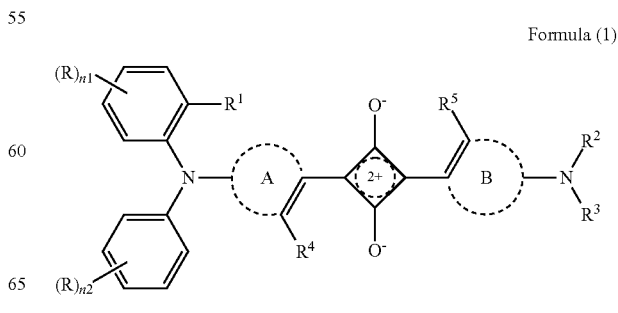

Formula (1)

In Formula (1), a ring A and a ring B each respectively represent an aromatic hydrocarbon ring which may have a substituent. $R^1$ represents an alkyl group, a cycloalkyl group, an aromatic hydrocarbon group, or a halogen atom. $R^2$ and $R^3$ each respectively represent an alkyl group or a cycloalkyl group. R represents a substituent. $R^1$ and R, or two Rs may be combined with each other to form a ring. $R^4$ and $R^5$ each respectively represent a hydroxy group or an amino group. n1 and n2 each respectively represent an integer of 0 to 4.

2. The squarylium compound according to item 1, wherein the compound having a structure represented by Formula (1) is a compound having a structure represented by Formula (2).

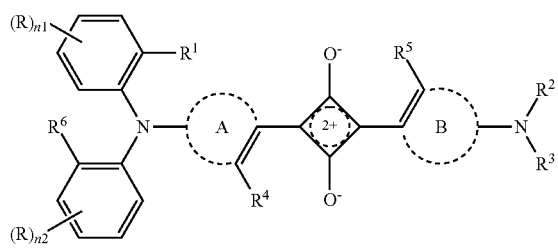

Formula (2)

In Formula (2), a ring A and a ring B each respectively represent an aromatic hydrocarbon ring which may have a substituent. $R^1$ and $R^6$ each respectively represent an alkyl group, a cycloalkyl group, an aromatic hydrocarbon group, or a halogen atom. $R^2$ and $R^3$ each respectively represent an alkyl group or a cycloalkyl group. R represents a substituent. $R^1$ and R, $R^6$ and R, or two Rs may be combined with each other to form a ring. $R^4$ and $R^5$ each respectively represent a hydroxy group or an amino group. n1 and n2 each respectively represent an integer of 0 to 4.

3. The squarylium compound according to item 1, wherein the compound having a structure represented by Formula (1) is a compound having a structure represented by Formula (3).

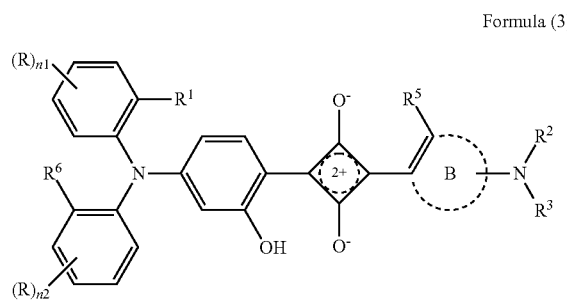

Formula (3)

In Formula (3), a ring B represents an aromatic hydrocarbon ring which may have a substituent. $R^1$ and $R^6$ each respectively represent an alkyl group, a cycloalkyl group, an aromatic hydrocarbon group, or a halogen atom. $R^2$ and $R^3$ each respectively represent an alkyl group or a cycloalkyl group. R represents a substituent. $R^1$ and R, $R^6$ and R, or two Rs may be combined with each other to form a ring. $R^5$ represents a hydroxy group or an amino group. n1 and n2 each respectively represent an integer of 0 to 4.

4. The squarylium compound according to item 1, wherein the compound having a structure represented by Formula (1) is a compound having a structure represented by Formula (4).

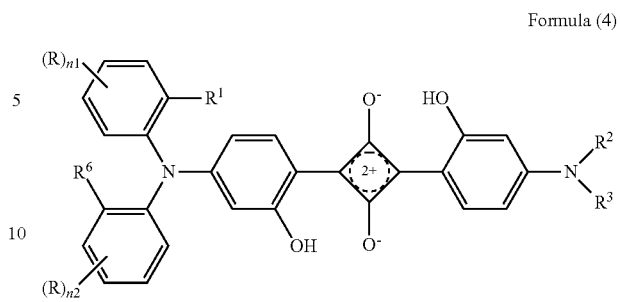

Formula (4)

In Formula (4), $R^1$ and $R^6$ each respectively represent an alkyl group, a cycloalkyl group, an aromatic hydrocarbon group, or a halogen atom. $R^2$ and $R^3$ each respectively represent an alkyl group or a cycloalkyl group. R represents a substituent. $R^1$ and R, $R^6$ and R, or two Rs may be combined with each other to form a ring. n1 and n2 each respectively represent an integer of 0 to 4.

5. A light-emitting composition containing the squarylium compound according to any one of items 1 to 4.

6. A light-emitting film containing the squarylium compound according to any one of items 1 to 4.

Effects of the Invention

By the above means of the present invention, it is possible to provide a novel squarylium compound capable of emitting near-infrared light having high luminous efficiency, particularly little decrease in luminous efficiency in a solid film, and excellent light resistance. In addition, it is possible to provide a light-emitting composition and a light-emitting film each containing the squarylium compound.

Although the expression mechanism or the action mechanism of the effect of the present invention has not been clarified, it is inferred as follows. The squarylium compound has a structure composed of a squaric acid skeleton showing strong electron acceptability and an amino group showing squarylium donor property, and exhibits a sharp absorption/emission peak and a high molar extinction coefficient in the red to near-infrared region. A typical squarylium compound R-3 and optical properties ($\lambda_{max}^{PL}$: maximum emission wavelength, $\Phi f$: emission quantum yield, molar extinction coefficient (log$\varepsilon$)) are shown below.

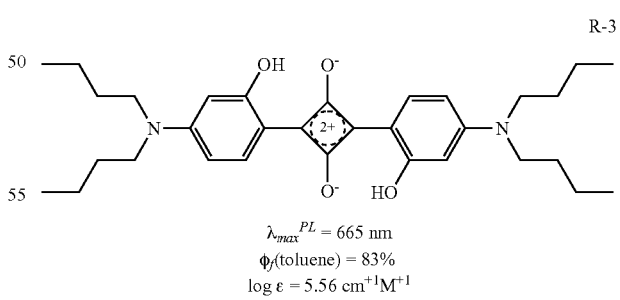

R-3

$\lambda_{max}^{PL} = 665$ nm
$\Phi_f$(toluene) = 83%
log $\varepsilon$ = 5.56 cm$^{+1}$M$^{+1}$ However, the squarylium compound has a high n-planarity and a zwitterionic structure in which cations and anions coexist in the same molecule, so that it easily aggregates. As a result, it has been known that when viewed as a luminescent material, although it shows a high emission quantum yield in a solution, it aggregates in a solid film and the emission quantum yield decreases.

On the other hand, since the squarylium compound of the present invention has at least one substituent at the ortho position of the arylamine, the arylamine and the squaric acid skeleton are twisted, and the n-planarity of the molecule is lowered. Therefore, the interaction between the squarylium compounds and the interaction of the squarylium compound with the dispersant are suppressed. As a result, it is considered that quenching due to aggregation is unlikely to occur even in the film and the luminescence does not decrease.

Further it was found that the emission quantum yield was improved by the aromatic hydrocarbon ring substituted with an amino group having a strong electron donating property. This is because the squarylium compound has a structure composed of a squaric acid skeleton exhibiting electron acceptor properties and an amino group exhibiting electron donor properties. As a result, when a donor having strong electron donor properties is used, it is presumed that light emission based on intramolecular charge transfer transition will occur.

In addition, the squarylium compound of the present invention has an effect of being superior in light resistance to conventional squarylium compounds. Since the compound of the present invention has little heat deactivation from the excited state, decomposition due to heat is suppressed, and aggregation is suppressed, so that decomposition due to aggregation is suppressed. Therefore, it is presumed that the reaction between molecules due to the approach of molecules is suppressed, and the absorption spectrum does not become broad and light in a larger wavelength range is not absorbed as observed in the aggregate.

EMBODIMENTS TO CARRY OUT THE INVENTION

The squarylium compound of the present invention is characterized by having a structure represented by Formula (1). This feature is a technical feature common to or corresponding to each of the following embodiments (forms). In an embodiment of the present invention, from the viewpoint of expressing the effect of the present invention, it is preferable that the compound having the structure represented by Formula (1) is a compound having a structure represented by Formula (2).

Further, it is preferable that the compound having the structure represented by Formula (1) is a compound having a structure represented by Formula (3). And further, it is preferable that the compound having the structure represented by Formula (1) is a compound having a structure represented by Formula (4). It is preferable that the light-emitting composition and the light-emitting film contain the squarylium compound of the present invention.

Hereinafter, the present invention and the constitution elements thereof, as well as configurations and embodiments to carry out the present invention, will be detailed in the following. In the present description, when two figures are used to indicate a range of value before and after "to", these figures are included in the range as a lowest limit value and an upper limit value.

Hereinafter, the squarylium compound, the light-emitting composition, and the light-emitting film of the present invention will be described, but the present invention is not limited thereto.

<<Squarylium Compound>>
[Squarylium Compound Having a Structure Represented by Formulas (1) to (4)]

The squarylium compound of the present invention receives excitation energy from the outside, transits to a singlet excited state, and then emits fluorescence when returning to the ground state. Further, since this compound exhibits a high molar extinction coefficient, it is excellent in light emission by photoexcitation and light emission by Forster-type energy transfer. Furthermore, it was found that this compound was excellent in light resistance. The emission color of the squarylium compound of the present invention is a near-infrared light color. Specifically, the maximum emission wavelength in the fluorescence spectrum of this compound is in the range of 650 to 1000 nm.

The squarylium compound of the present invention has a structure represented by the following Formula (1).

Formula (1)

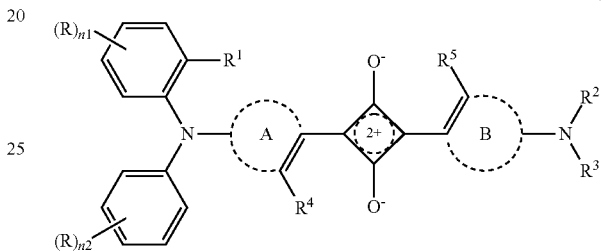

In Formula (1), a ring A and a ring B each respectively represent an aromatic hydrocarbon ring which may have a substituent. $R^1$ represents an alkyl group, a cycloalkyl group, an aromatic hydrocarbon group, or a halogen atom. $R^2$ and $R^3$ each respectively represent an alkyl group or a cycloalkyl group. R represents a substituent. $R^1$ and R, or two Rs may be combined with each other to form a ring. $R^4$ and $R^5$ each respectively represent a hydroxy group or an amino group. n1 and n2 each respectively represent an integer of 0 to 4.

The aromatic hydrocarbon ring (it may be called as "an aromatic hydrocarbon ring group", "an aromatic carbon ring group", or "an aryl group") represented by a ring A and a ring B is a substituted or unsubstituted aromatic hydrocarbon ring having 6 to 18 carbon atoms. Examples thereof are a phenyl group, a naphthyl group, an anthryl group, a fluorenyl group, a phenanthryl group, and a biphenylyl group. Preferably, a phenyl group, a naphthyl group, and an anthryl group may be mentioned.

The alkyl group represented by $R^1$ is a substituted or unsubstituted alkyl group having 1 to 10 carbon atoms. Examples thereof are a methyl group, an ethyl group, a propyl group, an isopropyl group, a butyl group, an isobutyl group, a pentyl group, a hexyl group, an octyl group, and a dodecyl group. Examples of the cycloalkyl group represented by $R^1$ are a cyclopentyl group and a cyclohexyl group.

The aromatic hydrocarbon group represented by $R^1$ is a substituted or unsubstituted aromatic hydrocarbon group having 6 to 18 carbon atoms. Examples thereof are a phenyl group, a naphthyl group, an anthryl group, a fluorenyl group, a phenanthryl group, and a biphenylyl group. Preferably, a phenyl group and a naphthyl group may be mentioned.

Examples of the halogen atom represented by $R^1$ include a fluorine atom, a chlorine atom, and a bromine atom.

Examples of the substituent that may be possessed by the ring A and the ring B in Formula (1), or represented by R in Formula (1) are as follows: an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group); a cycloalkyl group (for example, a cyclopentyl group and a cyclohexyl group); an alkenyl group (for example, a vinyl group and an allyl group); an alkynyl group (for example, an ethynyl group and a propargyl group); an aromatic hydrocarbon group (for example, a phenyl group, a p-chlorophenyl group, a mesityl group, a tolyl group, a xylyl group, a naphthyl group, an anthryl group, an azulenyl group, an acenaphthenyl group, a fluorenyl group, a phenantolyl group, an indenyl group, a pyrenyl group, and a biphenylyl group); an aromatic heterocyclic group (for example, a pyridyl group, a a pyrimidinyl group, a furyl group, a pyrrolyl group, an imidazolyl group, a benzimidazolyl group, a pyrazolyl group, a pyrazinyl group, a triazolyl group (for example, 1,2,4-triazol-1-yl group, and 1,2,3-triazol-1-yl group), a pyrazolotriazolyl group, an oxazolyl group, a benzoxazolyl group, a thiazolyl group, an isoxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolynyl group, a diazacarbazolyl group (indicating a ring structure in which one of the carbon atoms constituting the carboline ring of the carbolynyl group is replaced with a nitrogen atom), a quinoxalinyl group, a pyridazinyl group, a triazinyl group, a quinazolinyl group, and a phthalazinyl group); a heterocyclic group (for example, a pyrrolidyl group, an imidazolidyl group, a morpholyl group, and an oxazolidyl group); an alkoxy group (for example, a methoxy group, an ethoxy group, a propyloxy group, a pentyloxy group, an hexyloxy group, an octyloxy group, and a dodecyloxy group); a cycloalkoxy group (for example, a cyclopentyloxy group, and a cyclohexyloxy group); an aryloxy group (for example, a phenoxy group and a naphthyloxy group); an alkylthio group (for example, a methylthio group, an ethylthio group, a propylthio group, a pentylthio group, hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group and a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethyl carbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethyhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethymexylaminocarbonyl group, a dodecylaminocarbonyl group, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-pyridylaminoureido group); a sulfinyl group (for example, a methylsulfinyl group, an ethylsufinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsulfinyl group); an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group); an arylsulfonyl group or a heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a dodecylamino group, an anilino group, a naphthylamino group, and a 2-pyridylamino group); a halogen atom (for example, a fluorine atom, a chlorine atom, and a bromine atom); a fluorinated hydrocarbon group (for example, a fluoromethyl group, trifluoromethyl group, a pentafluoroethyl group, and a pentafluorophenyl group); a cyano group; a nitro group; a hydroxy group; a mercapto group; a silyl group (for example, a trimethylsilyl group, a triisopropylsilyl group, a triphenylsilyl group, and a phenyldiethylsilyl group) and a phosphono group. Preferred examples include an alkyl group, an aromatic hydrocarbon group, an amino group, a hydroxy group and a silyl group. Further, these substituents may be further substituted by the above-mentioned substituents.

The number of substituents in the Formula (1) is not particularly limited. When there are two or more substituents, the substituents may be the same or different from each other. Adjacent substituents may be bonded to each other to form a cyclic structure. For example, $R^1$ and R, $R^2$ and $R^3$, two Rs, $R^5$ and $R^2$, or $R^5$ and $R^3$ may be combined with each other to form a ring.

The cyclic structure formed by the adjacent substituents may be an aromatic ring or an alicyclic ring, may contain a hetero atom, and the cyclic structure may be a fused ring having two or more rings. The hetero atom referred to here is preferably one selected from the group consisting of a nitrogen atom, an oxygen atom and a sulfur atom. Examples of the formed ring structure include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isooxazole ring, a thiazole ring, an isothiazole ring, a cyclohexadiene ring, a cyclohexene ring, a cyclopentaene ring, a cycloheptatriene ring, a cycloheptadiene ring, a cycloheptaene ring, a carbazole ring, and a dibenzofuran ring.

$R^2$ an $R^3$ each respectively represent an alkyl group or a cycloalkyl group. Examples of the alkyl group include a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group. Examples of the cycloalkyl group include a cyclopentyl group and a cyclohexyl group.

Examples of the cases where $R^2$ and $R^3$ are bonded to each other to form a ring include a piperidine ring and a morpholine ring. $R^2$ and $R^3$ may be further substituted with the substituents described above.

$R^4$ and $R^5$ each respectively represent a hydroxy group or an amino group. The amino group is a substituted or unsubstituted amino group, but is preferably an unsubstituted amino group. n1 and n2 each respectively represent an integer of 0 to 4, and 0 or 1 is preferable.

The squarylium compound represented by Formula (1) is preferably a compound having a structure represented by the following Formula (2).

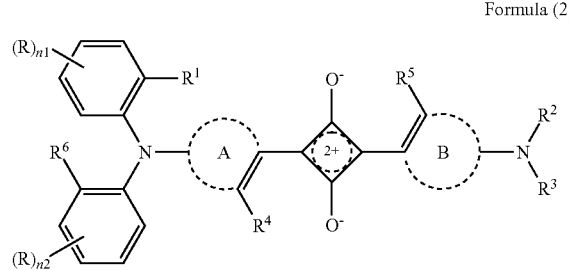

Formula (2)

In Formula (2), a ring A and a ring B each respectively represent an aromatic hydrocarbon ring which may have a substituent. $R^1$ and $R^6$ each respectively represent an alkyl group, a cycloalkyl group, an aromatic hydrocarbon group, or a halogen atom. $R^2$ and $R^3$ each respectively represent an alkyl group or a cycloalkyl group. R represents a substituent. $R^1$ and R, $R^6$ and R, or two Rs may be combined with each other to form a ring. $R^4$ and $R^5$ each respectively represent a hydroxy group or an amino group. n1 and n2 each respectively represent an integer of 0 to 4.

In Formula (2), a ring A and a ring B each represent an aromatic hydrocarbon ring which may have a substituent as in Formula (1). $R^1$ and $R^6$ each respectively represent an alkyl group, a cycloalkyl group, an aromatic hydrocarbon group or a halogen atom as $R^1$ of Formula (1). R represents a substituent as in Formula (1), and $R^1$ and R, $R^6$ and R, or two Rs may be bonded to each other to form a ring. $R^4$ and $R^5$ each represent a hydroxy group or an amino group as in Formula (1). n1 and n2 each respectively represent an integer of 0 to 4, and 0 or 1 is preferable. Further, it is preferable that the compound represented by Formula (1) is a compound having a structure represented by the following Formula (3).

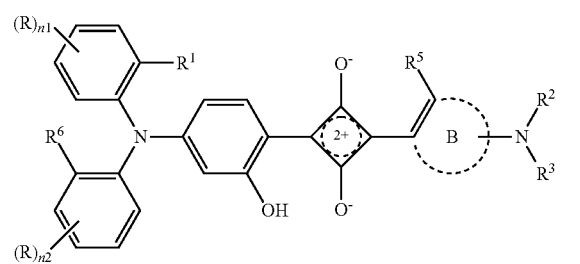

Formula (3)

In Formula (3), a ring B represents an aromatic hydrocarbon ring which may have a substituent. $R^1$ and $R^6$ each respectively represent an alkyl group, a cycloalkyl group, an aromatic hydrocarbon group, or a halogen atom. $R^2$ and $R^3$ each respectively represent an alkyl group or a cycloalkyl group. R represents a substituent. $R^1$ and R, $R^6$ and R, or two Rs may be combined with each other to form a ring. $R^5$ represents a hydroxy group or an amino group. n1 and n2 each respectively represent an integer of 0 to 4.

In Formula (3), the ring B, $R^1$, $R^6$, $R^2$, $R^3$, $R^5$, R, n1 and n2 are synonymous with the ring B, $R^1$, $R^6$, $R^2$, $R^3$, $R^5$, R, n1 and n2 in Formula (2). Further, it is preferable that the compound represented by Formula (1) is a compound having a structure represented by the following Formula (4).

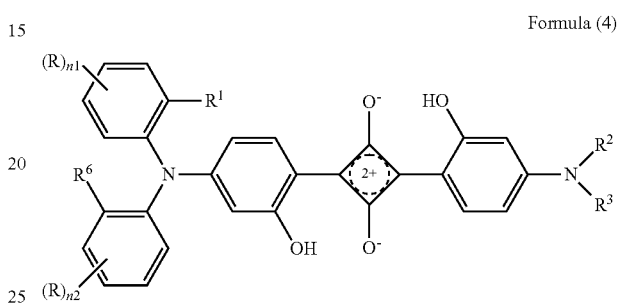

Formula (4)

In Formula (4), $R^1$ and $R^6$ each respectively represent an alkyl group, a cycloalkyl group, an aromatic hydrocarbon group, or a halogen atom. $R^2$ and $R^3$ each respectively represent an alkyl group or a cycloalkyl group. R represents a substituent. $R^1$ and R, $R^6$ and R, or two Rs may be combined with each other to form a ring. n1 and n2 each respectively represent an integer of 0 to 4. In Formula (4), $R^1$, $R^6$, $R^2$, $R^3$, R, n1 and n2 are synonymous with $R^1$, $R^6$, $R^2$, $R^3$, R, n1 and n2 in Formula (2). The following are examples of the squarylium compound having a structure represented by Formulas (1), (2), (3) and (4) of the present invention, but the present invention is not limited thereto.

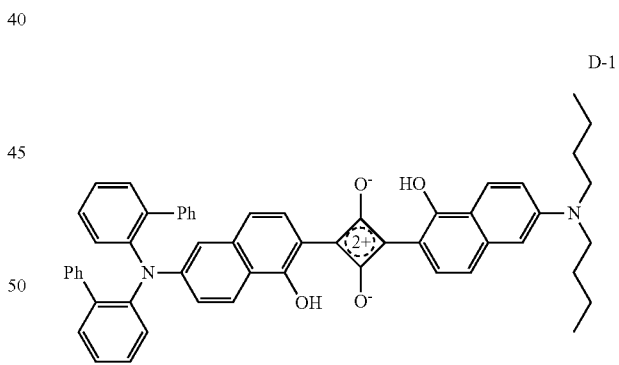

D-1

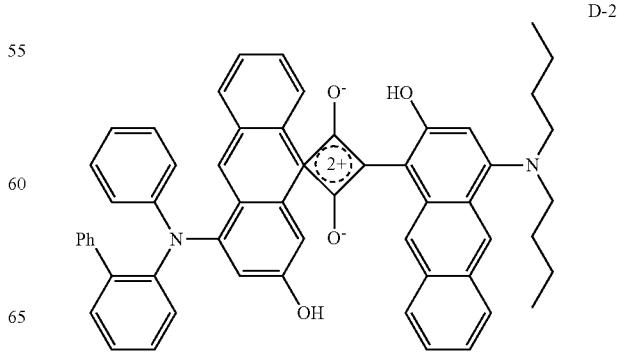

D-2

-continued
D-3
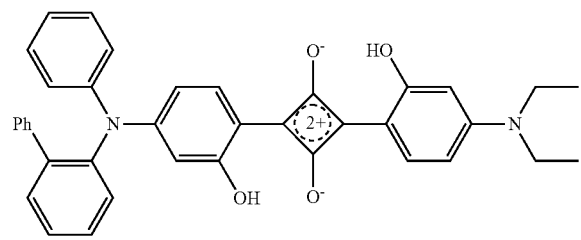
D-4
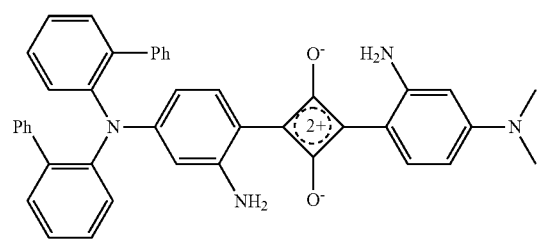
D-5
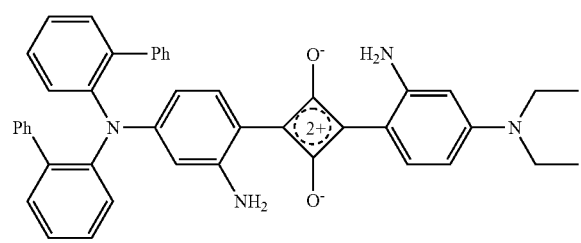
D-6
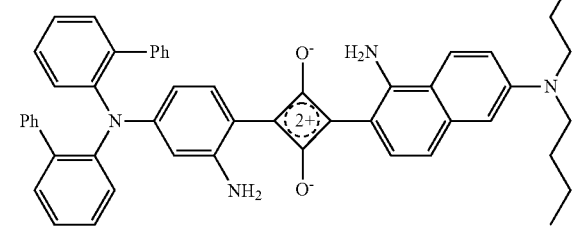
D-7
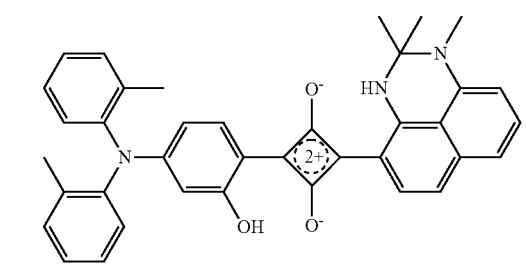
-continued
D-8
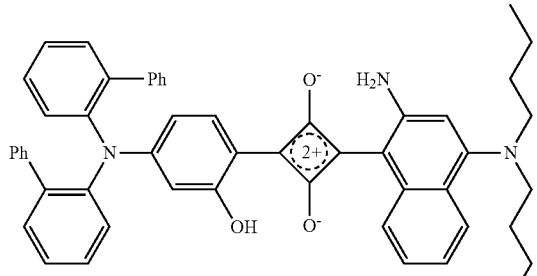
D-9
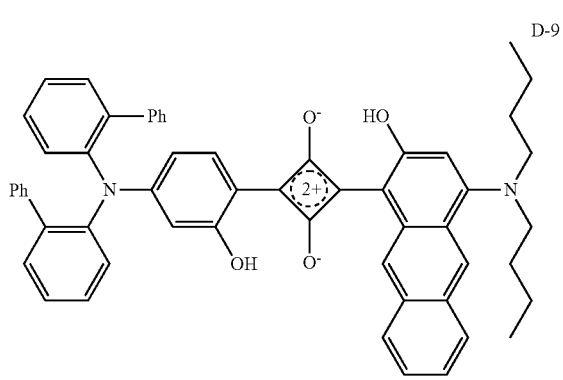
D-10
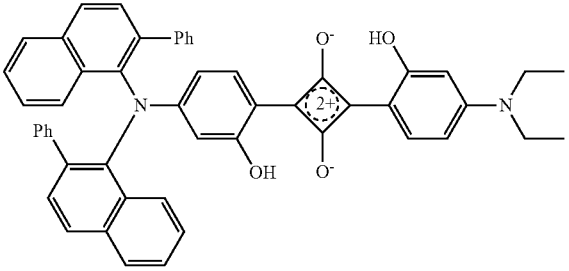
D-11
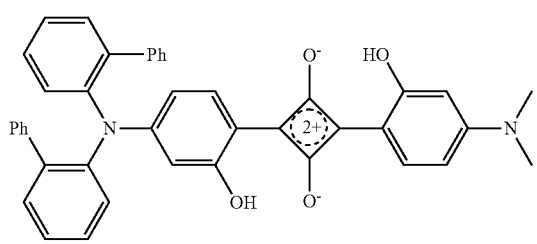
D-12
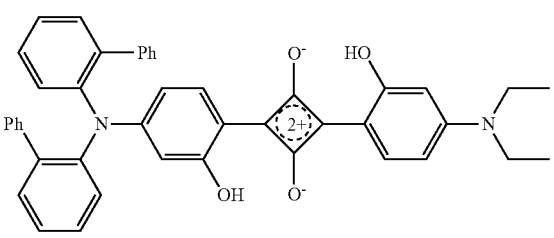

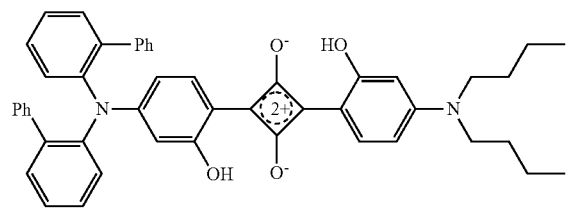
D-13
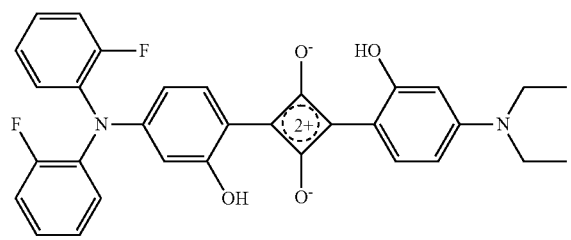
D-19
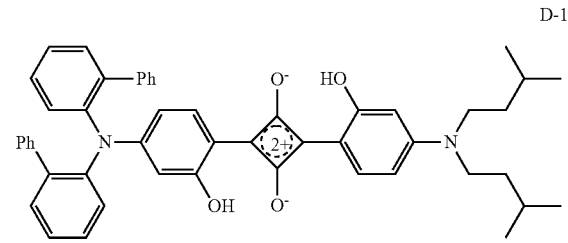
D-14
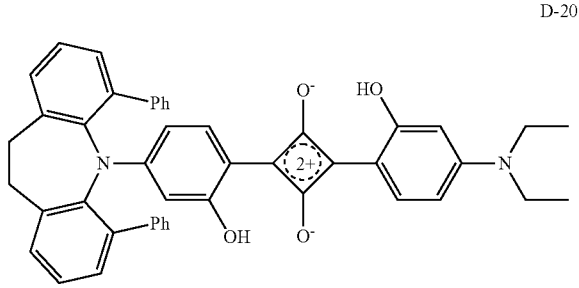
D-20
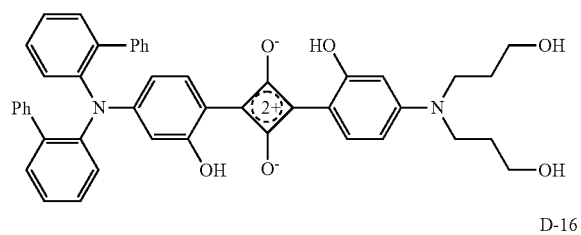
D-15
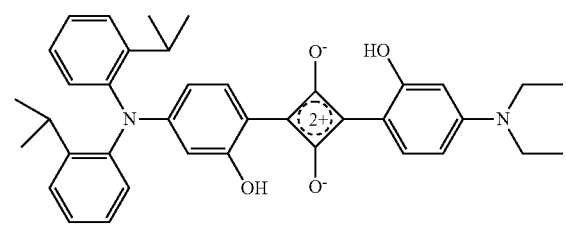
D-21
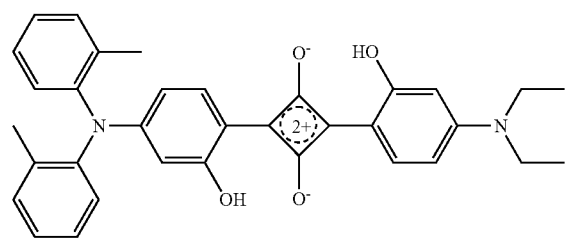
D-16
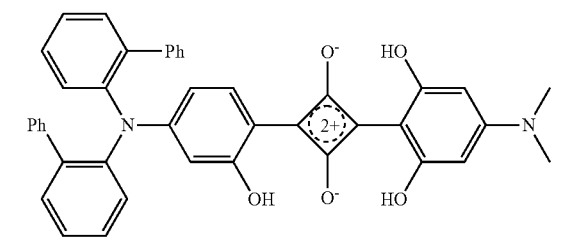
D-22
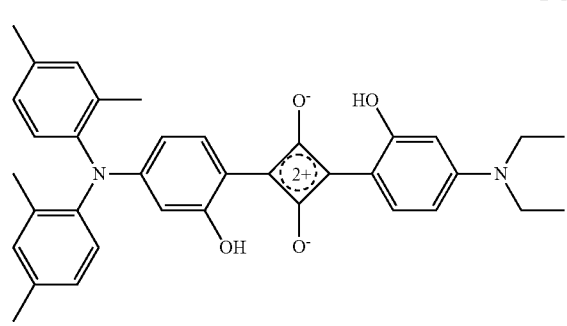
D-17
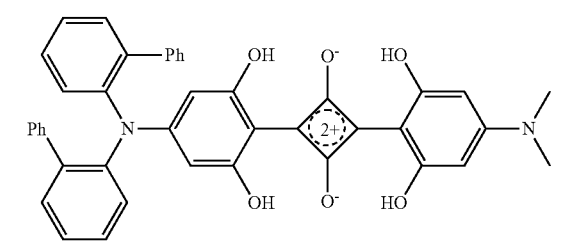
D-23
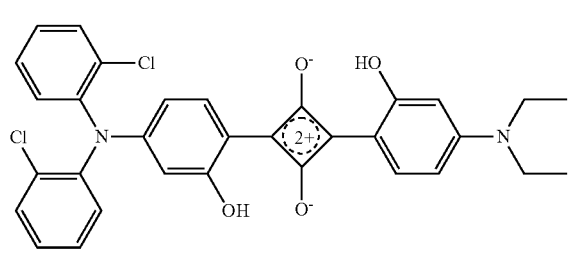
D-18
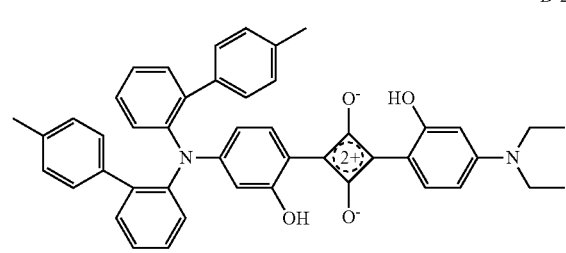
D-24

-continued

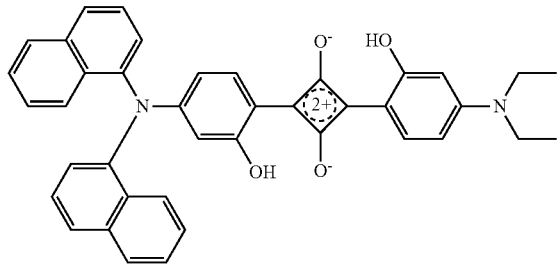

D-25

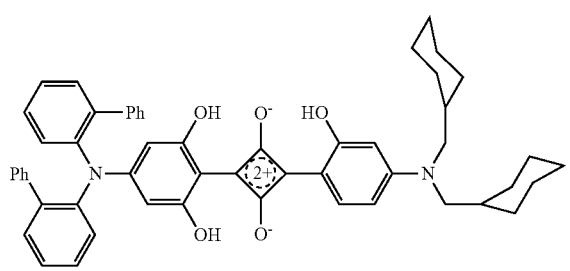

D-26

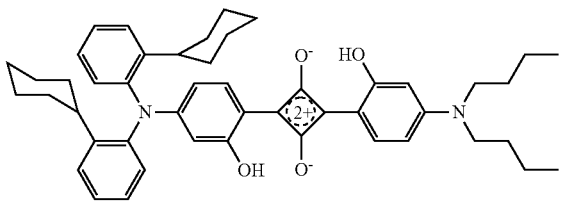

D-27

<Synthetic Method>
The squarylium compound of the present invention may be synthesized with the method described in Chemistry of Materials, Vol. 23, p. 4789 (2011) and The Journal of Physical Chemistry, Vol. 91, p. 5184 (1987), for example. Or it may be synthesized by referring to the method described in the reference documents described in these documents. As an example, a synthetic example of the exemplary compound D-12 is shown below.

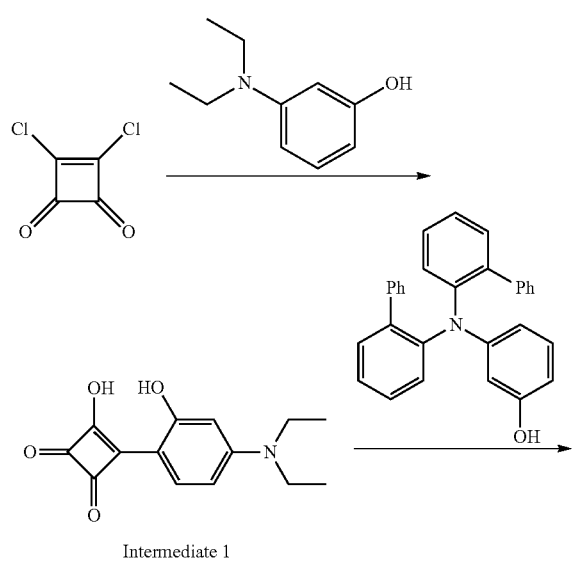

Intermediate 1

-continued

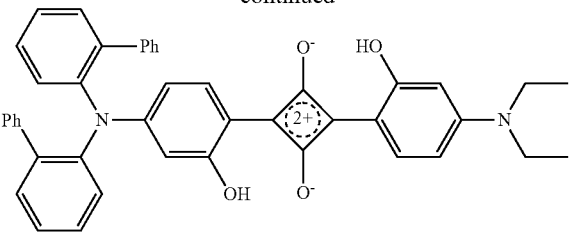

D-12

1,2-Dichloro-1-cyclobutene-3,4-dione (25.0 g, 0.17 mol) and N,N-diethyl-3-aminophenol (24.6 g, 0.15 mol) were added to a mixed solution of acetic acid (250 mL) and water (250 mL), and the mixture was stirred with heating under reflux for 2 hours. The product was purified by column chromatography to give 10.5 g of an intermediate 1. Next, the intermediate 1 (2.59 g, 9.91 mol) and 3-(di([1,1'-biphenyl]-2-yl)amino)phenol (4.10 g, 9.91 mol) were added to a mixed solvent of toluene (80 mL) and normal butanol (40 mL) to dissolve. The mixture was stirred with heating under reflux for 24 hours. The product was purified by column chromatography to obtain 1.20 g of a targeted exemplary compound (D-12).

(Measurement of Fluorescence Spectrum)

The emission color of the squarylium compound of the present invention may be confirmed by the following method. The content of the squarylium compound of the present invention is adjusted to $10^{-6}$ M in a toluene solution, and the fluorescence spectrum of this sample is measured at room temperature (300 K). Fluorescence Spectrophotometer F7000 manufactured by Hitachi High-Tech Corporation is used to measure the emission spectrum. Then, when the maximum emission wavelength (wavelength having the maximum emission intensity; also referred to as "emission peak wavelength") is in the range of 650 to 1000 nm, it is determined to be a near-infrared color.

<<Light-Emitting Composition and Light-Emitting Film>>

The light-emitting composition of the present invention is characterized by containing the squarylium compound of the present invention. The light-emitting composition of the present invention is preferably used as a composition in which a dispersant is added to a squarylium compound for obtaining film formation stability, or as a composition in which a solvent is further added. Further, the light-emitting film of the present invention is characterized by containing the squarylium compound of the present invention. Specifically, it may be produced by forming the light-emitting composition of the present invention in a film form.

Examples of the dispersant are a (meth)acrylate resin, a polyester resin, a polyamide resin, a polyimide resin, a polystyrene resin, a polyepoxy resin, a polyester resin, an amino resin, a fluorine resin, a phenol resin, a polyurethane resin, a polyethylene resin, a polypropylene resin, a polyvinyl chloride resin, a polyvinyl alcohol resin, a polyether resin, a polyether ketone resin, a polyphenylene sulfide resin, a polycarbonate resin, and an aramid resin. Among them, preferable are a polystyrene resin, a polyethylene resin, a polypropylene resin, and a polyvinyl chloride resin. Moreover, the copolymers of these are also preferable.

The (meth)acrylate resin is synthesized by homopolymerizing or copolymerizing various methacrylate monomers or acrylate monomers, and by changing the monomer species and the monomer composition ratio, the desired (meth)acrylate may be obtained.

Examples of a monomer component that forms a (meth) acrylate resin used in the present invention are as follows. (Meth)acrylic acid, methyl (meth)acrylate, ethyl (meth)acrylate, propyl (meth)acrylate, butyl (meth)acrylate, isopropyl (meth)acrylate, isobutyl (meth)acrylate, t-butyl (meth)acrylate, stearyl (meth)acrylate, 2-hydroxyethyl (meth)acrylate, acetoacetoxyethyl (meth)acrylate, dimethylaminoethyl (meth)acrylate, 2-hydroxypropyl (meth)acrylate, di(ethylene glycol) ethyl ether (meth)acrylate, ethyleneglycol methyl ether (meth)acrylate, isobonyl (meth)acrylate, ethyltrimethylammonium chloride (meth)acrylate, trifluoroethyl (meth)acrylate, octafluoropentyl (meth)acrylate, 2-acetamidomethyl (meth)acrylate, 2-methoxyethyl (meth)acrylate, 2-dimethylaminoethyl (meth)acrylate, 3-trimethoxysilanepropyl (meth)acrylate, benzyl (meth)acrylate, tridecyl (meth)acrylate, 4-hydroxybutyl (meth)acrylate, tetrahydrofurfuryl (meth)acrylate, dodecyl (meth)acrylate, octadecyl (meth)acrylate, 2-diethylaminoethyl (meth)acrylate, 2-ethylhexyl (meth)acrylate, cyclohexyl (meth)acrylate, phenyl (meth)acrylate, and glycidyl (meth)acrylate may be mentioned. Among them, preferable are (meth)acrylic acid, methyl (meth)acrylate, ethyl (meth)acrylate, propyl (meth) acrylate, butyl (meth)acrylate, stearyl (meth)acrylate, 2-hydroxyethyl (meth)acrylate, acetoacetoxyethyl (meth)acrylate, benzyl (meth)acrylate, tridecyl (meth)acrylate, dodecyl (meth)acrylate, and 2-ethylhexyl (meth)acrylate.

The polystyrene resin includes a homopolymer of a styrene monomer, or a random copolymer, a block copolymer, or a graft copolymer obtained by copolymerizing another monomer having an unsaturated double bond copolymerizable with the styrene monomer. Further included are blends and polymer alloys in which such polymers are blended with other polymers. Examples of the styrene monomer include: a nucleus alkyl substituted styrene such as styrene, α-methylstyrene, α-ethylstyrene, α-methylstyrene-p-methylstyrene, o-methylstyrene, m-methylstyrene, and p-methylstyrene; and a nucleus halogen substituted styrene such as o-chlorstyrene, m-chlorstyrene, p-chlorstyrene, p-bromostyrene, dichlorostyrene, dibromostyrene, trichlorostyrene, and tribromostyrene. Among them, styrene and α-methylstyrene are preferred.

Examples of the resin used in the present invention by homopolymerizing or copolymerizing these monomers include: a copolymer resin of benzyl methacrylate/ethyl acrylate or butyl acrylate, a copolymer resin of methyl methacrylate/2-ethylhexyl methacrylate, and a copolymer resin of methyl methacrylate/methacrylate/stearyl methacrylate/acetoacetoxyethyl methacrylate, a copolymer resin of styrene/acetoacetoxyethyl methacrylate/stearyl methacrylate, a copolymer resin of styrene/2-hydroxyethyl methacrylate/stearyl methacrylate, and a copolymer resin of 2-ethylhexyl methacrylate/2-hydroxyethyl methacrylate.

Further, when the squarylium compound of the present invention is used as a luminescent material for an organic EL element, a known host compound may be used as a dispersant. Specific examples thereof include compounds described in the following documents, but the present invention is not limited thereto: Japanese Patent Application Publication (JP-A) Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084, and 2002-308837, US Patent Application Publication Nos. 2003/01755553, 2006/0280965, 2005/0112407, 2009/0017330, 2009/0030202, and 2005/0238919, WO Nos. 2001/039234, 2009/021126, 2008/056746, 2004/093207, 2005/089025, 2007/0637996, 2007/063754, 2004/107822, 2005/030900, 2006/114966, 2009/086028, 2009/003898, and 2012/023947, JP-A No. 2008-074939, JP-A No. 2007-254297, European Patent No. 2034538, WO No. 2011/055933, WO No. 2012/035853, and JP-A No. 2015-38941.

Regarding the content of the luminescent material in the light-emitting composition and the light-emitting film of the present invention, the preferable lower limit is 0.001 parts by mass and the preferable upper limit is 50 parts by mass with respect to 100 parts by mass of the dispersant. When the content of the luminescent material is within this range, it has high transparency and may display a high-luminance image by being irradiated with light. A more preferable lower limit of the content of the luminescent material is 0.01 parts by mass, a more preferable upper limit is 10 parts by mass, a further preferable lower limit is 0.05 parts by mass, a further preferable upper limit is 8 parts by mass, and a particularly preferable lower limit is 0.1 parts by mass, a particularly preferable upper limit is 5 parts by mass.

[Emission Quantum Yield]

The emission quantum yield is expressed as the ratio of the number of emitted photons to the number of absorbed photons. If all the excited molecules return to the ground state by fluorescence, the emission quantum yield will be 1, but in reality it will not be 1 due to non-radiative deactivation.

Non-radiative deactivation is a transition that returns to the ground state without emitting fluorescence. In addition to relaxation to the triplet state by intersystem crossing, there are internal conversions in which the energy of the electronic state is converted into vibration energy and finally becomes thermal energy, and energy transfer that transfers energy to other molecules.

Assuming that the rate constants of the fluorescence transition and the non-radiation transition of the excited molecule are Kf and Knr, respectively, the emission quantum yield $\Phi$ (%) is represented by the following.

$$\Phi(\%) = (Kf/(Kf+Knr)) \times 100$$

Therefore, in order to improve the emission quantum yield, it is necessary to suppress the non-radiative deactivation of the excited molecule.

In the present invention, in order to suppress non-radiative deactivation, the squarylium compound has at least one substituent at the ortho position of the arylamine. This substituent lowers the n-planarity of the molecule and may suppress the aggregation between the molecules. As a result, it is presumed that the quenching caused by aggregation becomes smaller and the luminescence is improved.

EXAMPLES

Hereinafter, the present invention will be specifically described with reference to examples, but the present invention is not limited thereto. In the examples, the indication of "parts" or "%" is used, but unless otherwise specified, it indicates "parts by mass" or "% by mass".

Example 1

The compound used in a comparative example is shown below.

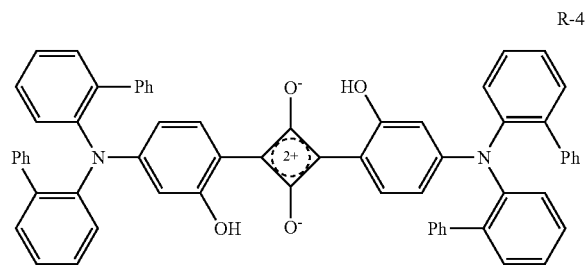

R-4

<Measurement of Quantum Yield>

With respect to squarylium compounds of the present invention D-1, D-3, D-5, D-6, D-7, D-10, D-12, D-17, D-21 and D-26, comparative compounds R-1 and R-4, the emission quantum yields in the solution and in the film were measured by the following methods, respectively.

(1) Evaluation of Luminescence Quantum Yield in Solution

The squarylium compound of the present invention or the comparative compound was dissolved in toluene so as to have a concentration of $10^{-6}$ M. The emission quantum yield of the obtained solution was measured using an absolute PL quantum yield measuring device (C11347 manufactured by Hamamatsu Photonics K.K.).

(2) Evaluation of Emission Quantum Yield in the Film

CBP (4,4'-N,N'-dicarbazolebiphenyl) and the squarylium compound of the present invention or the comparative compound were dissolved in chloroform so as to be contained at a ratio of 99.5% by mass and 0.5% by mass, respectively. The obtained solution was applied onto a quartz substrate by a spin coating method at 500 rpm for 30 seconds to form a thin film, and then dried at 50° C. for 30 minutes. The absolute PL quantum yield of the obtained thin film was measured using an absolute PL quantum yield measuring device (C11347 manufactured by Hamamatsu Photonics K.K.) and used as the emission quantum yield in the film. In Table I, the luminescence quantum yield of D-1 in the solution is shown as a relative value of 100.

(Light Resistance)

The film prepared under the same conditions as the measurement of emission quantum yield was covered with glass, and the decrease in absorption intensity at the maximum absorption wavelength from the sample after exposure to sunlight for 1 week with respect to the unexposed sample was calculated by the residual rate. The evaluation was made according to the following criteria. A spectrophotometer (U-3300 manufactured by Hitachi High-Tech Corporation) was used to measure the absorption intensity at the maximum absorption wavelength.

Residual rate (%)=(Maximum absorption wavelength intensity of exposed sample/Maximum absorption wavelength intensity of unexposed sample)×100

AA: Residual rate is 90% or more
BB: Residual rate is 80% or more and less than 90%
CC: Residual rate is less than 80%
Practically, a residual rate of 90% or more is preferable. The above evaluation results are shown in Table I.

It should be noted that the exemplary compounds D-1, D-3, D-5, D-6, D-7, D-10, D-12, D-17, D-21 and D-26, which are the squarylium compounds of the present invention, were confirmed that they have a maximum emission wavelength in the near-infrared region of 700 to 850 nm in toluene. For the measurement, the above-mentioned Fluorescence Spectrophotometer F7000 manufactured by Hitachi High-Tech Corporation was used.

TABLE I

| Measurement sample | Emission quantum yield (Relative value) | | Light resistance | Remarks |
| --- | --- | --- | --- | --- |
| | In solution | In film | | |
| D-1 | 100 | 97 | BB | Present Invention |
| D-3 | 103 | 105 | BB | Present Invention |
| D-5 | 100 | 97 | BB | Present Invention |
| D-6 | 114 | 111 | AA | Present Invention |
| D-7 | 114 | 108 | AA | Present Invention |
| D-10 | 121 | 119 | AA | Present Invention |
| D-12 | 130 | 127 | AA | Present Invention |
| D-17 | 122 | 124 | AA | Present Invention |
| D-21 | 127 | 122 | AA | Present Invention |
| D-26 | 124 | 125 | AA | Present Invention |
| R-1 | 41 | 29 | CC | Comparative Example |
| R-4 | 90 | 86 | BB | Comparative Example |

From Table I, it can be seen that the squarylium compound of the present invention has high luminous efficiency and excellent light resistance.

INDUSTRIAL APPLICABILITY

The squarylium compound of the present invention emits near-infrared light having high luminous efficiency, particularly little decrease in luminous efficiency in a solid film, and excellent light resistance. It is possible to use it for infrared cameras, bioimaging, biosensing, and infrared communication.

What is claimed is:

1. A squarylium compound having a structure represented by Formula (1),

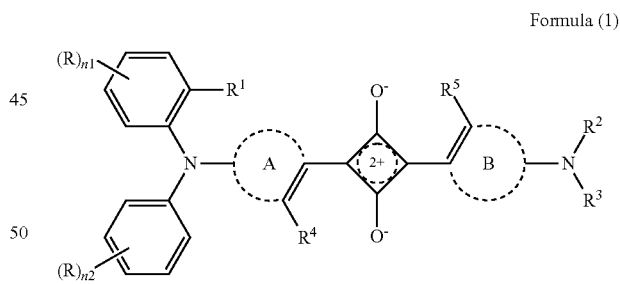

Formula (1)

in Formula (1), a ring A and a ring B each respectively represent an aromatic hydrocarbon ring which may have a substituent; $R^1$ represents an alkyl group, a cycloalkyl group, an aromatic hydrocarbon group, or a halogen atom; $R^2$ and $R^3$ each respectively represent an alkyl group or a cycloalkyl group; R represents a substituent; $R^1$ and R, or two Rs may be combined with each other to form a ring; $R^4$ and $R^5$ each respectively represent a hydroxy group or an amino group; and n1 and n2 each respectively represent an integer of 0 to 4.

2. The squarylium compound described in claim 1, wherein the compound having a structure represented by Formula (1) is a compound having a structure represented by Formula (2),

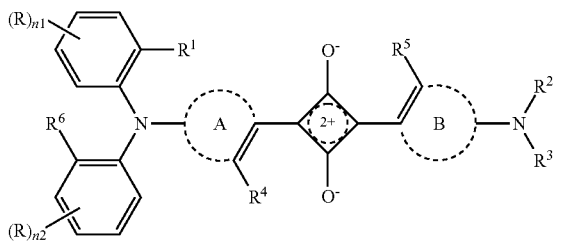

Formula (2)

in Formula (2), a ring A and a ring B each respectively represent an aromatic hydrocarbon ring which may have a substituent; $R^1$ and $R^6$ each respectively represent an alkyl group, a cycloalkyl group, an aromatic hydrocarbon group, or a halogen atom; $R^2$ and $R^3$ each respectively represent an alkyl group or a cycloalkyl group; R represents a substituent; $R^1$ and R, $R^6$ and R, or two Rs may be combined with each other to form a ring; $R^4$ and $R^5$ each respectively represent a hydroxy group or an amino group; and n1 and n2 each respectively represent an integer of 0 to 4.

3. The squarylium compound described in claim 1, wherein the compound having a structure represented by Formula (1) is a compound having a structure represented by Formula (3),

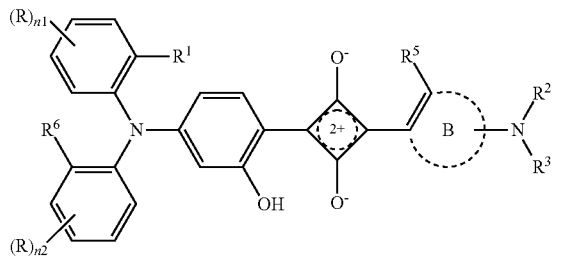

Formula (3)

in Formula (3), a ring B represents an aromatic hydrocarbon ring which may have a substituent; $R^1$ and $R^6$ each respectively represent an alkyl group, a cycloalkyl group, an aromatic hydrocarbon group, or a halogen atom; $R^2$ and $R^3$ each respectively represent an alkyl group or a cycloalkyl group; R represents a substituent; $R^1$ and R, $R^6$ and R, or two Rs may be combined with each other to form a ring; $R^5$ represents a hydroxy group or an amino group; and n1 and n2 each respectively represent an integer of 0 to 4.

4. The squarylium compound described in claim 1, wherein the compound having a structure represented by Formula (1) is a compound having a structure represented by Formula (4),

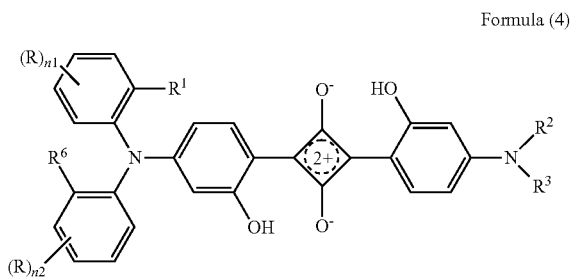

Formula (4)

in Formula (4), $R^1$ and $R^6$ each respectively represent an alkyl group, a cycloalkyl group, an aromatic hydrocarbon group, or a halogen atom; $R^2$ and $R^3$ each respectively represent an alkyl group or a cycloalkyl group; R represents a substituent; $R^1$ and R, $R^6$ and R, or two Rs may be combined with each other to form a ring; and n1 and n2 each respectively represent an integer of 0 to 4.

5. A light-emitting composition containing the squarylium compound described in claim 1.

6. A light-emitting film containing the squarylium compound described in claim 1.

* * * * *